(12) United States Patent
Weeber et al.

(10) Patent No.: US 8,740,978 B2
(45) Date of Patent: Jun. 3, 2014

(54) INTRAOCULAR LENS HAVING EXTENDED DEPTH OF FOCUS

(75) Inventors: Hendrik A. Weeber, Groningen (NL);
Patricia Ann Piers, Groningen (NL);
Carina R. Reisin, Tustin, CA (US)

(73) Assignee: AMO Regional Holdings, Quarryvale (IE)

( * ) Notice: Subject to any disclaimer, the term of this patent is extended or adjusted under 35 U.S.C. 154(b) by 0 days.

(21) Appl. No.: 12/120,201

(22) Filed: May 13, 2008

(65) Prior Publication Data

US 2009/0234448 A1 Sep. 17, 2009

Related U.S. Application Data

(60) Provisional application No. 60/968,250, filed on Aug. 27, 2007.

(51) Int. Cl.
*A61F 2/16* (2006.01)

(52) U.S. Cl.
USPC .......................... 623/6.3; 623/6.27

(58) Field of Classification Search
USPC ............... 623/6.24, 6.27–6.31, 6.37
See application file for complete search history.

(56) References Cited

U.S. PATENT DOCUMENTS

| | | |
|---|---|---|
| 3,367,734 A | 2/1968 | Bystricky et al. |
| 4,637,697 A | 1/1987 | Freeman |
| 4,642,112 A | 2/1987 | Freeman |
| 4,655,565 A | 4/1987 | Freeman |
| 4,778,462 A | 10/1988 | Grendahl |
| 4,795,462 A | 1/1989 | Grendahl |
| 4,798,608 A | 1/1989 | Grendahl |
| 4,798,609 A | 1/1989 | Grendahl |
| 4,932,970 A | 6/1990 | Portney |
| 4,995,714 A | 2/1991 | Cohen |
| 4,995,715 A | 2/1991 | Cohen |
| 5,016,977 A | 5/1991 | Baude et al. |
| 5,056,908 A | 10/1991 | Cohen |
| 5,066,301 A | 11/1991 | Wiley |
| 5,089,023 A | 2/1992 | Swanson |

(Continued)

FOREIGN PATENT DOCUMENTS

| | | |
|---|---|---|
| EP | 343067 A1 | 11/1989 |
| EP | 457553 A2 | 11/1991 |

(Continued)

OTHER PUBLICATIONS

U.S. Appl. No. 11/618,325, filed Dec. 29, 2006 (Brady et al.).

(Continued)

*Primary Examiner* — David H Willse
*Assistant Examiner* — Tiffany Shipmon
(74) *Attorney, Agent, or Firm* — AMO Regional Holdings

(57) ABSTRACT

An ophthalmic lens for providing enhanced or extended depth of focus includes an optic having an aperture disposed about an optical axis. The optic includes a first surface having a first shape and an opposing second surface having a second shape, the first and second surfaces providing, a base power and, in some embodiments an add power. The optic further includes an extended focus mask disposed upon at least one of the first shape and the second shape that is configured to provide the enhanced or extended depth of focus for one or more foci of the optic, as compared to a similar optic not having the extended focus mask.

15 Claims, 6 Drawing Sheets

(56) References Cited

U.S. PATENT DOCUMENTS

| | | | |
|---|---|---|---|
| 5,096,285 A | 3/1992 | Silberman | |
| 5,114,220 A | 5/1992 | Baude et al. | |
| 5,117,306 A | 5/1992 | Cohen | |
| 5,120,120 A | 6/1992 | Cohen | |
| 5,121,979 A | 6/1992 | Cohen | |
| 5,121,980 A | 6/1992 | Cohen | |
| 5,144,483 A | 9/1992 | Cohen | |
| 5,225,858 A | 7/1993 | Portney | |
| 5,225,997 A | 7/1993 | Lang | |
| 5,229,797 A | 7/1993 | Futhey et al. | |
| 5,652,638 A | 7/1997 | Roffman et al. | |
| 5,699,142 A | 12/1997 | Lee et al. | |
| 5,748,282 A | 5/1998 | Freeman | |
| 5,760,871 A | 6/1998 | Kosoburd et al. | |
| 5,796,462 A | 8/1998 | Roffman et al. | |
| 5,968,094 A | 10/1999 | Werblin et al. | |
| 6,126,283 A | 10/2000 | Wen et al. | |
| 6,126,286 A | 10/2000 | Portney | |
| 6,142,625 A | 11/2000 | Sawano et al. | |
| 6,210,005 B1 | 4/2001 | Portney | |
| 6,338,559 B1 | 1/2002 | Williams et al. | |
| 6,457,826 B1 | 10/2002 | Lett | |
| 6,464,355 B1 | 10/2002 | Gil | |
| 6,474,814 B1 | 11/2002 | Griffin | |
| 6,488,708 B2 | 12/2002 | Sarfarazi | |
| 6,491,721 B2 | 12/2002 | Freeman et al. | |
| 6,527,389 B2 | 3/2003 | Portney | |
| 6,533,416 B1 | 3/2003 | Fermigier et al. | |
| 6,536,899 B1 | 3/2003 | Fiala | |
| 6,537,317 B1 | 3/2003 | Steinert et al. | |
| 6,547,822 B1 | 4/2003 | Lang | |
| 6,554,859 B1 | 4/2003 | Lang et al. | |
| 6,557,992 B1 | 5/2003 | Dwyer et al. | |
| 6,609,793 B2 | 8/2003 | Norrby et al. | |
| 6,705,729 B2 | 3/2004 | Piers et al. | |
| 6,808,262 B2 | 10/2004 | Chapoy et al. | |
| 6,830,332 B2 | 12/2004 | Piers et al. | |
| 6,846,326 B2 * | 1/2005 | Zadno-Azizi et al. | 623/6.34 |
| 6,851,803 B2 | 2/2005 | Wooley et al. | |
| 6,923,539 B2 * | 8/2005 | Simpson et al. | 351/160 R |
| 6,923,540 B2 | 8/2005 | Ye et al. | |
| 6,986,578 B2 | 1/2006 | Jones | |
| 7,036,931 B2 | 5/2006 | Lindacher et al. | |
| 7,048,760 B2 * | 5/2006 | Cumming | 623/6.37 |
| 7,061,693 B2 * | 6/2006 | Zalevsky | 359/738 |
| 7,073,906 B1 | 7/2006 | Portney | |
| 7,137,702 B2 | 11/2006 | Piers et al. | |
| 7,156,516 B2 | 1/2007 | Morris et al. | |
| 7,188,949 B2 | 3/2007 | Bandhauer et al. | |
| 7,287,852 B2 | 10/2007 | Fiala | |
| 7,293,873 B2 | 11/2007 | Dai et al. | |
| 7,365,917 B2 | 4/2008 | Zalevsky | |
| 7,377,640 B2 | 5/2008 | Piers et al. | |
| 7,441,894 B2 | 10/2008 | Zhang et al. | |
| 7,475,986 B2 | 1/2009 | Dai et al. | |
| 7,615,073 B2 | 11/2009 | Deacon et al. | |
| 7,871,162 B2 | 1/2011 | Weeber | |
| 2002/0118337 A1 | 8/2002 | Perrott et al. | |
| 2003/0076478 A1 | 4/2003 | Cox | |
| 2003/0171808 A1 * | 9/2003 | Phillips | 623/6.37 |
| 2004/0021824 A1 | 2/2004 | Ye et al. | |
| 2004/0085515 A1 | 5/2004 | Roffman et al. | |
| 2004/0106992 A1 | 6/2004 | Lang et al. | |
| 2004/0111153 A1 * | 6/2004 | Woods et al. | 623/6.37 |
| 2004/0150789 A1 | 8/2004 | Jones | |
| 2004/0156014 A1 | 8/2004 | Piers et al. | |
| 2004/0230299 A1 | 11/2004 | Simpson et al. | |
| 2005/0096226 A1 | 5/2005 | Stock et al. | |
| 2005/0128432 A1 | 6/2005 | Altmann | |
| 2005/0203619 A1 | 9/2005 | Altmann | |
| 2005/0267575 A1 | 12/2005 | Nguyen et al. | |
| 2006/0009816 A1 | 1/2006 | Fang et al. | |
| 2006/0030938 A1 | 2/2006 | Altmann | |
| 2006/0034003 A1 | 2/2006 | Zalevsky | |
| 2006/0055883 A1 | 3/2006 | Morris et al. | |
| 2006/0066808 A1 | 3/2006 | Blum et al. | |
| 2006/0098162 A1 * | 5/2006 | Bandhauer et al. | 351/159 |
| 2006/0098163 A1 | 5/2006 | Bandhauer et al. | |
| 2006/0109421 A1 | 5/2006 | Ye et al. | |
| 2006/0116763 A1 | 6/2006 | Simpson | |
| 2006/0116764 A1 * | 6/2006 | Simpson | 623/6.23 |
| 2006/0176572 A1 | 8/2006 | Fiala | |
| 2006/0238702 A1 | 10/2006 | Glick et al. | |
| 2006/0244904 A1 | 11/2006 | Hong et al. | |
| 2007/0052920 A1 | 3/2007 | Stewart et al. | |
| 2007/0129803 A1 | 6/2007 | Cumming et al. | |
| 2007/0171362 A1 | 7/2007 | Simpson et al. | |
| 2007/0182924 A1 * | 8/2007 | Hong et al. | 351/171 |
| 2008/0030677 A1 | 2/2008 | Simpson | |
| 2008/0161913 A1 | 7/2008 | Brady et al. | |
| 2008/0161914 A1 | 7/2008 | Brady et al. | |
| 2009/0062911 A1 | 3/2009 | Bogaert | |
| 2009/0164008 A1 | 6/2009 | Hong et al. | |
| 2009/0187242 A1 | 7/2009 | Weeber et al. | |
| 2009/0210054 A1 | 8/2009 | Weeber et al. | |
| 2009/0268155 A1 | 10/2009 | Weeber | |
| 2009/0268158 A1 | 10/2009 | Weeber | |
| 2009/0295295 A1 | 12/2009 | Shannon et al. | |
| 2009/0323020 A1 | 12/2009 | Zhao et al. | |
| 2010/0016961 A1 | 1/2010 | Hong et al. | |
| 2010/0161048 A1 | 6/2010 | Schaper, Jr. | |

FOREIGN PATENT DOCUMENTS

| | | |
|---|---|---|
| EP | 681198 A1 | 11/1995 |
| EP | 0926531 A1 | 6/1999 |
| EP | 949529 A2 | 10/1999 |
| EP | 1424049 A1 | 6/2004 |
| EP | 1310267 B1 | 1/2008 |
| EP | 1424049 B1 | 6/2009 |
| WO | 92/22264 | 12/1992 |
| WO | WO9303409 A1 | 2/1993 |
| WO | WO0019906 A1 | 4/2000 |
| WO | WO0163344 A1 | 8/2001 |
| WO | WO0182839 A1 | 11/2001 |
| WO | WO0189424 A1 | 11/2001 |
| WO | WO0221194 A2 | 3/2002 |
| WO | WO03009053 A1 | 1/2003 |
| WO | WO2004034129 A1 | 4/2004 |
| WO | WO2004090611 A1 | 10/2004 |
| WO | WO2004096014 A2 | 11/2004 |
| WO | WO2005019906 A1 | 3/2005 |
| WO | WO2006025726 A1 | 3/2006 |
| WO | 2006/047698 A1 | 5/2006 |
| WO | WO2006060477 A2 | 6/2006 |
| WO | WO2006060480 A2 | 6/2006 |
| WO | 2007/092948 A1 | 8/2007 |
| WO | 2007/133384 A2 | 11/2007 |
| WO | WO2008045847 A2 | 4/2008 |
| WO | WO2009076670 A1 | 6/2009 |

OTHER PUBLICATIONS

U.S. Appl. No. 11/618,411, filed Dec. 29, 2006 (Brady et al.).

Cohen, Practical design of a bifocal hologram contact lens or intraocular lens, Applied Optics, (1992), 3750-3754, 31(19).

Liou et al, Anatomically accurate, finite model eye for optical modeling, J. Opt. Soc. Am. A, (Aug. 1997), 1684-1695, 14(8).

Marsack et al, Metrics of optical quality derived from wave aberrations predict visual performance, Journal of Vision, (2004), 322-328, vol. 4.

Van Meeteren, Calculations on the optical modulation transfer function of the human eye for white light, Optica Acta, (1974), 395-412, 21(5).

Villegas et al., Correlation between optical and psychophysical parameters as a function of defocus, Optometry and Vision Science, (2002), 60-67, 79(1).

"Diffractive lenses for extended depth of focus and presbyopic correction." Presentation from Wavefront Congress held on Feb. 15, 2008, in Rochester, New York.

Marsack J.D. et al., "Metrics of Optical Quality Derived from Wave Aberrations Predict Visual Performance", J. Vis, (4), pp. 322-328 (2004).

(56) References Cited

OTHER PUBLICATIONS

Villegas E.A. et al., "Correlation between Optical and Psychophysical Parameters as a Function of Defocus", Optom Vis. Sci, 79 (1) pp. 60-67 (2002).

Van Meeteren A., "Calculations on the Optical Modulation Transfer Function of the Human Eye for White Light", Optica Acta 21 (5) pp. 395-412 (1974).

Cohen A.L., "Practical design of a Bifocal Hologram Contact Lens or Intraocular Lens", Applied Optics 31 (19) pp. 3750-3754 (1992).

Liou H.L. et al., "Anatomically Accurate, Finite Model Eye for Optical Modeling", J. Opt. Sco. Am. A vol. 14(8) pp. 1684-1695 (1997).

Alfonso J.F., et al., "Prospective Study of the Acri.LISA bifocal Intraocular Lens," Journal of Cataract Refractive Surgery, 2007, vol. 33 (11), pp. 1930-1935.

Canovas C., et al., "Hybrid Adaptive-Optics Visual Simulator," Optical Letters, 2010, vol. 35 (2), pp. 196-198.

Doskolovich L.L., et al., "Special Diffractive Lenses," SPIE, 1992, vol. 1780, pp. 393-402.

International Search Report for Application No. PCT/EP2008/061235, mailed on Mar. 5, 2009, 4 pages.

International Search Report for Application No. PCT/EP2009/051783, mailed on Apr. 28, 2009, 3 pages.

International Search Report for Application No. PCT/US09/042449, mailed on Nov. 5, 2009, 5 pages.

International Search Report for Application No. PCT/US2010/038167, mailed on Sep. 27, 2010, 2 pages.

Monsoriu J.A., et al., "Devil's Lenses," Optics Express, 2007, vol. 15, (21), pp. 13858-13864.

Norrby S., et al., "Model Eyes for Evaluation of Intraocular Lenses," Applied Optics, 2007, vol. 46 (26), pp. 6595-6605.

Piers P.A., et al., "Theoretical Comparison of Aberration-Correcting Customized and Aspheric Intraocular Lenses," Journal of Refractive Surgery, 2007, vol. 23 (4), pp. 374-384.

Siedlecki D., et al., "Radial Gradient index Intraocular Lens: a Theoretical Model," Journal of Modern Optics, 2008, vol. 55 (4-5), pp. 639-647.

Vanden Berg T.J., "Analysis of Intraocular Straylight, Especially in Relation to Age," Optometry and Vision Science, 1995, vol. 72 (2), pp. 52-59.

International Search Report and Written Opinion for Application No. PCT/IB2011/001067, mailed on Sep. 13, 2011, 13 pages.

Piers P.A., et al., "Eye Models for the Prediction of Contrast Vision in Patients with New Intraocular Lens Designs," Optics Letters, 2004, vol. 29 (7), pp. 733-735.

Terwee T., et al., "Visualization of the Retinal Image in an Eye Model With Spherical and Aspheric, Diffractive, and Refractive Multifocal Intraocular Lenses," Journal of Refractive Surgery, 2008, vol. 24 (3), pp. 223-232.

Co-pending U.S. Appl. No. 12/771,550, filed Apr. 30, 2010.

International Search Report for Application No. PCT/IB2009/005590, mailed on Sep. 30, 2009, 3 pages.

International Search Report for Application No. PCT/US08/073999, mailed on Dec. 3, 2008, 3 pages.

International Search Report for Application No. PCT/US2010/061081, mailed on Apr. 6, 2011, 2 pages.

U.S. Appl. No. 12/129,155, filed Apr. 23, 2009.

U.S. Appl. No. 12/109,251, filed Apr. 24, 2008.

Co-pending U.S. Appl. No. 12/503,267, filed Jul. 15, 2009.

De Almeida M.S., et al., "Different Schematic Eyes and their Accuracy to the in Vivo Eye: A Quantitative Comparison Study," Brazilian Journal of Physics, 2007, vol. 37 (2A), 10 pages.

\* cited by examiner

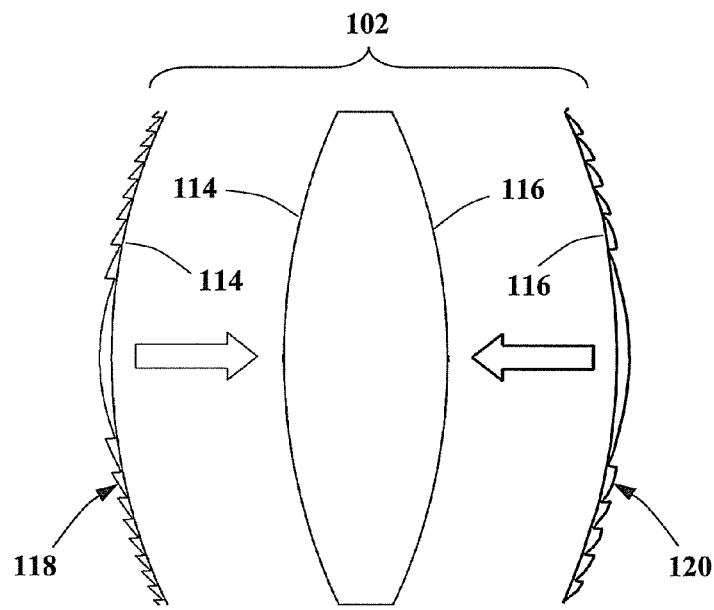
FIG. 2
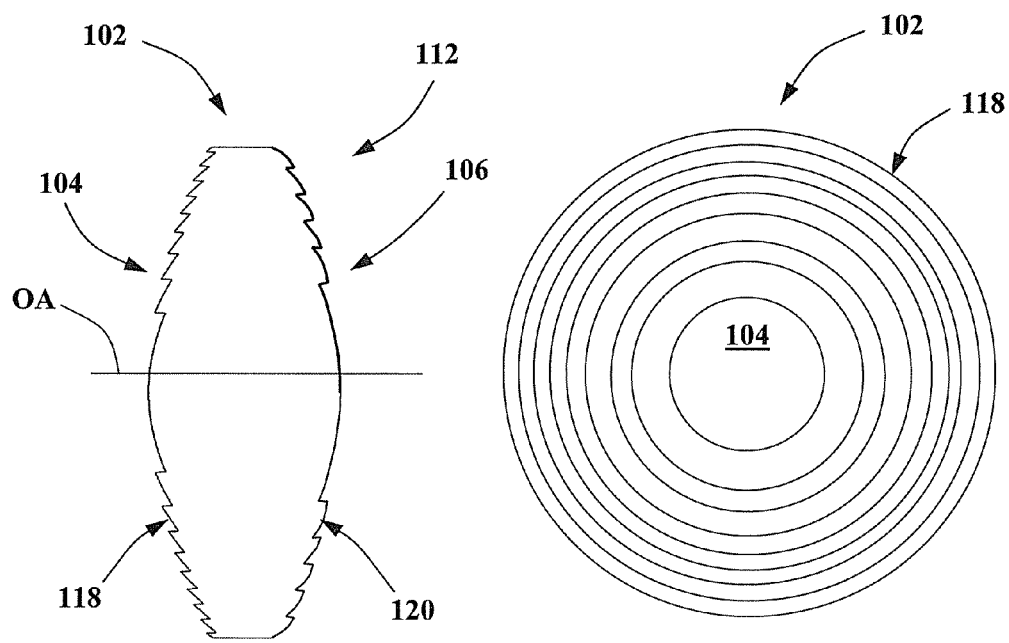
FIG. 3
FIG. 4

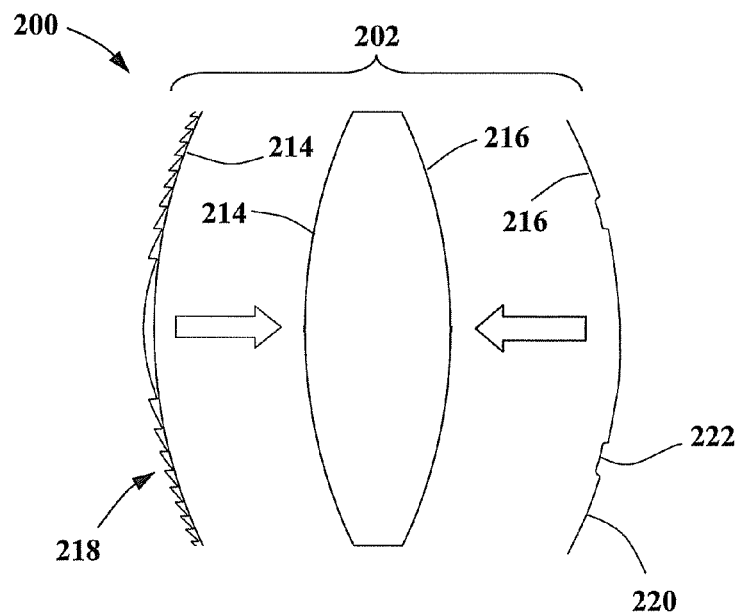
FIG. 7
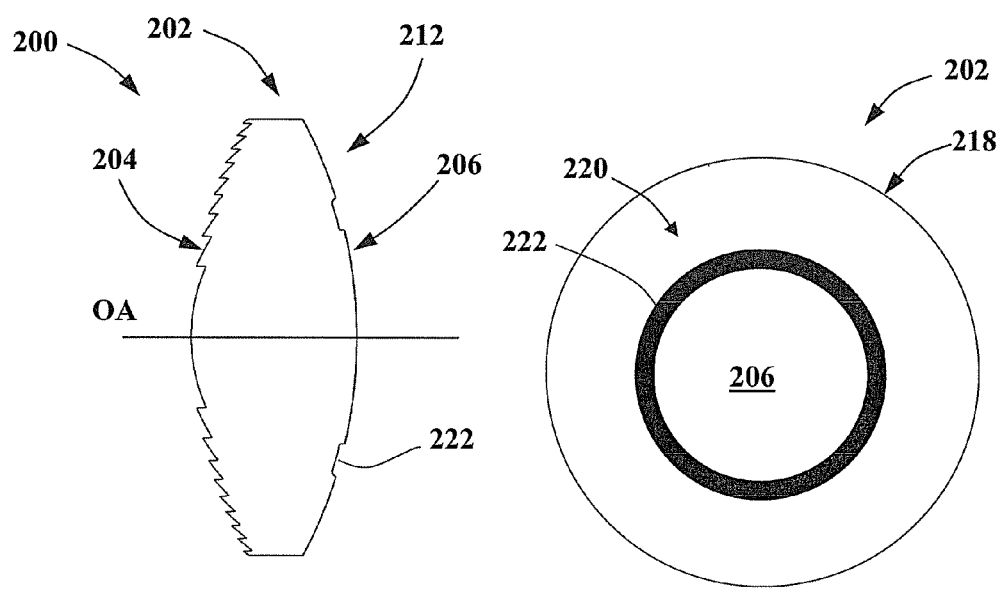
FIG. 8
FIG. 9

INTRAOCULAR LENS HAVING EXTENDED DEPTH OF FOCUS

RELATED APPLICATION

The present application claims priority under 35 U.S.C. §119(e) to provisional application No. 60/968,250, filed on Aug. 27, 2007, and is herein incorporated in its entirety.

BACKGROUND OF THE INVENTION

1. Field of the Invention

The present invention relates generally to intraocular lenses and more specifically to intraocular lenses having an extended depth of focus.

2. Description of the Related Art

Intraocular lenses are commonly used to replace the natural lens of the eye when it become cataractous. Alternatively, the natural lens may be replaced to correct other visual conditions, for example, to provide accommodation or pseudo-accommodation when a subject develops presbyopia and is not longer able to focus on both distant objects and near objects. In any event, accommodating and/or multifocal intraocular lenses may be used to restore at least some degree of accommodative and/or pseudo-accommodative ability.

Accommodating intraocular lenses are configured to focus on objects over a range of distances by moving axially and/or by changing shape in response to an ocular force produced by the ciliary muscle, zonules, and/or capsular bag of the eye. One problem encountered with accommodating intraocular lenses is an inability to utilize the available ocular forces to produce the full accommodative range typical of a younger eye.

Multifocal intraocular lenses provide a pseudo-accommodation by simultaneously providing two or more foci, for example, one to provide distant vision and the other to provide near vision. Over time, patients with multifocal intraocular lenses generally learn to select the focus that provides the sharper image and to ignore any other blurred images. One problem with multifocal intraocular lenses is a relatively high degree of dysphotopsia (e.g., halos or glare) and reduced contrast sensitivity due to the continual presence of defocused light.

Another approach for providing some degree of simulated accommodation is to extend the depth of focus of a traditional monofocal lens so that objects over a broader range of distances are simultaneously resolve. Again, issues such as contrast sensitivity and reduced contrast sensitivity are typical. Examples of this approach are discuss in U.S. Pat. No. 6,126,286 (Portney), U.S. Pat. No. 6,923,539 (Simpson et al.), and U.S. Pat. No. 7,061,693 (Zalevsky).

Accommodating and multifocal intraocular lenses are needed with enhanced performance and increased design flexibility in addressing the variety of complex issues involved in providing vision to subjects over a wide range of object distances.

SUMMARY OF THE INVENTION

The present invention is generally directed to ophthalmic devices, systems, and methods for extending the depth of focus of a subject's vision. The ophthalmic device may be an intraocular lens, a contact lens, a corneal inlay or onlay, a pair of spectacles, or the like. Alternatively, the ophthalmic device may be a part of the or structure of a natural eye, for example, the resulting structure on a corneal surface produced by a refractive procedure such as a LASIK or PRK procedure. Embodiments of the present invention may find particular use in ophthalmic devices having a multifocal element (e.g., a diffractive or refractive lens producing two or more foci or images) or having accommodative capabilities.

In one aspect of the present invention, a lens for ophthalmic use, such as an intraocular lens, comprises an optic having an aperture disposed about an optical axis. The optic comprises a first surface having a first shape and an opposing second surface having a second shape. The optic further comprises an extended focus mask that is disposed on at least one of the shapes. The first and second surfaces provide a base power and an add power. The powers are selected to produce a first focus and a second focus when the intraocular lens is placed within an eye of a subject. At least one of the first focus and second focus have a depth of focus, when illuminated by a light source over the entire aperture, that is greater than a depth of focus of a reference optic without the extended focus mask. The reference optic may have an aperture equal to the aperture of the intraocular lens and at least one of a base power equal to the base power of the ophthalmic lens and an add power equal to the add power of the ophthalmic lens.

In another aspect of the present invention, an accommodating intraocular lens comprises an optic having an aperture disposed about an optical axis. The optic comprises a first surface having a first shape and an opposing second surface having a second shape. The intraocular lens further comprises an extended focus mask that is disposed on at least one of the shapes. The first and second surfaces provide a base power that is selected to produce a focus when the intraocular lens is placed within an eye of a subject. The intraocular lens has a depth of focus, when illuminated by a light source over the entire clear aperture, that is greater than the depth of focus of a reference optic without the extended focus mask. The reference optic may have a base power and a clear aperture that are substantially equal to that of the intraocular lens. The intraocular lens is configured, in response to an ocular force, to change the optical power of the base power by at least 1 Diopter.

BRIEF DESCRIPTION OF THE DRAWINGS

Embodiments of the present invention may be better understood from the following detailed description when read in conjunction with the accompanying drawings. Such embodiments, which are for illustrative purposes only, depict the novel and non-obvious aspects of the invention. The drawings include the following figures, with like numerals indicating like parts:

FIG. 2 is an exploded side view of a lens according to an embodiment of the present invention where individual profiles of anterior and posterior lens surfaces have been separated from their perspective base profiles for clarity.

FIG. 3 is a side view of the lens shown in FIG. 2 showing the resultant surface profiles of the anterior and posterior surfaces.

FIG. 4 is a front view of the lens shown in FIG. 2 showing echelettes of the anterior surface according to an embodiment of the present invention.

FIG. 7 is an exploded side view of a lens according to another embodiment of the present invention where individual profiles of anterior and posterior lens surfaces have been separated from their perspective base profiles for clarity.

FIG. 8 is a side view of the lens shown in FIG. 7 showing the resultant surface profiles of the anterior and posterior surfaces.

FIG. 9 is a rear view of the lens shown in FIG. 7 showing phase-affecting, non-diffractive mask according to an embodiment of the present invention.

DETAILED DESCRIPTION

Embodiments of the present invention are generally directed to multifocal and accommodating ophthalmic lenses having at least one extended depth of focus. Embodiments of the present invention will be illustrated for intraocular lenses; however, other types of lenses, particularly other types of ophthalmic lenses, are anticipated. Embodiments of the present invention may be utilized as pseudophakic intraocular lenses in which an intraocular lens replaces the natural lens, supplemental intraocular lenses in which an intraocular lens is combined with a previously implanted intraocular lens, or phakic intraocular lenses in which an intraocular lens supplements the natural lens of the eye (e.g., by implantation of an intraocular lens in front of the iris or in the sulcus of a subject eye). These include, but are not limited to, spectacles, contact lenses, corneal implants, and the like. Embodiments of the present invention may also be extended to ophthalmic procedures, for example, to corneal refractive surgical procedures such as LASIK or PRK.

Figure 1:
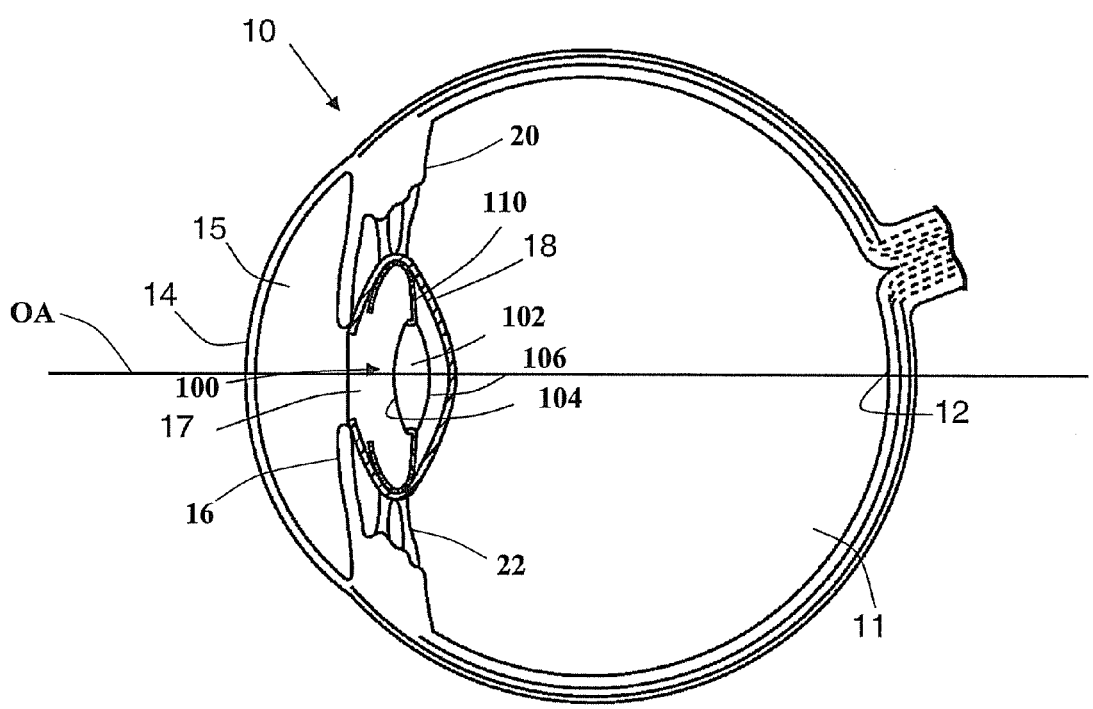
FIG. 1 is a schematic drawing of a human eye after implantation with an intraocular lens.

Referring to FIG. 1, in certain embodiments an intraocular lens 100 is implanted within an eye 10 of a subject such as a human patient. The eye 10 is generally disposed about an optical axis OA and includes a posterior segment 11, retina 12, a cornea 14, an anterior chamber 15, an iris 16, and a capsular bag 17 having a posterior wall 18. Prior to surgery, a natural lens occupies essentially the entire interior of the capsular bag 17. The eye 10 further comprises a ciliary muscle 20 and zonules 22 that transmit ocular forces produced by the ciliary muscle 20 to the capsular bag 17. Such ocular forces serve to provide accommodation in a phakic eye still containing the natural lens, for example, by deforming the natural lens to change its optical power.

After surgery, the capsular bag 17 houses the intraocular lens 100. The intraocular lens 100 is described in more detail below. Light enters from the left of FIG. 1 and is focused onto the retina 12 by the cornea 14 and the intraocular lens 100. After passing through the intraocular lens 100, light passes through the posterior segment 11, and strikes the retina 12, which detects the light and converts it to a signal transmitted through the optic nerve to the brain. The intraocular lens 100 includes an optic or optical element 102 that has a refractive index that is generally greater than the refractive index of the surrounding fluid. The optic 102 has an anterior surface 104 facing away from the retina 12 and a posterior surface 106 facing toward the retina 12, the surfaces 104, 106 are disposed about an optical axis OA. The optic 102 may be disposed adjacent to, and even pressed against, the posterior wall 18, for example, to reduce cellular growth on the optic 102 and the capsular bag 18. Alternatively, the optic 102 may be vaulted anteriorly toward the cornea 14, for example, so that the optic 100 moves away from the retina 12 in response to an ocular force on the intraocular lens 100.

The intraocular lens 100 and the optic 102 may be configured to provide accommodative or pseudo-accommodative vision. The optic 102 may be a bifocal or multifocal lens providing a plurality of focal lengths or optical powers, for example, a first focus or optical power to provide distant vision or intermediate vision and second focus or optical power to provide near or intermediate vision. The plurality of powers may be provided by either refractive and/or diffractive means. In some embodiments, a distribution between near and distant vision is constant or substantially constant over a variety of pupil sizes or lighting conditions. In other embodiments, the distribution between near and distant vision varies in a predetermined manner as the pupil size or lighting conditions vary, for example, as disclosed by Lee et al. in U.S. Pat. No. 5,699,142 or one of the Portney patents referenced herein.

Alternatively or additionally, the intraocular lens 100 and the optic 102 may be configured to provide accommodative power by deforming and/or moving the optic 102 along the optical axis OA in response to an ocular force. In some embodiments, the optic 102 may be a monofocal, bifocal, or multifocal lens. The optic 102 is attached to a positioning member or haptics 110, thereby operably coupling the optic 102 to the capsular bag 17. The haptics 110 are configured to transfer an ocular force to the optic 102 to provide accommodative movement or deformation. As used herein, an "ocular force" is typically a force produced by an eye to provide accommodation, for example, a force produce by the ciliary muscle, zonules, or capsular bag of an eye. An ocular force may generally be considered to be a force that is in a range from about 1 gram force to about 50 grams force, about 1 gram force to about 6 grams force or about 9 grams force, or from about 6 gram force to about 9 grams force. The difference in optical power between the farthest and nearest objects that may be brought into focus by a particular lens or lens system is known typically as the "accommodative range". A normal accommodative range is about 3 Diopter or about 4 Diopters at the plane of the optic 102, although this range may be extended to as high as 6 Diopters or more, depending on a subject's age, patient or doctor preference, the geometry of a patient's eye, and the like.

If the optic 102 is a bifocal or multifocal optic, then it may be characterized by a "base power" and at least one "add power". As used herein the term "base power" means a power (in Diopters) of an optic or lens required to provide distant vision at the retina of a subject eye. As used herein, the term "add power" means a difference in optical power (in Diopters) between a second power of the optic or lens and the base power. When the add power is positive, the sum of the add power and the base power corresponds to a total optical power suitable for imaging an object at some finite distance from the eye onto the retina. A typical maximum add power for an optic or lens is about 3 Diopter or about 4 Diopters in the plane of the lens, although this number may be as high as 6 or more Diopters (an intraocular lens add power of 4.0 Diopters is approximately equal to an increase in optical power of about 3.2 Diopters in a spectacle lens).

FIGS. 2 and 3 are side views of the intraocular lens 100 showing only the optic 102 and not the haptics 110. In certain embodiments the optic 102 has a clear aperture 112 that is disposed about the optical axis OA. As used herein, the term "clear aperture" means the opening of a lens or optic that restricts the extent of a bundle of light rays from a distant source that can be imaged or focused by the lens or optic. The clear aperture is typically circular and is specified by its diameter, although other shapes are acceptable, for example, oval, square, or rectangular. Thus, the clear aperture represents the full extent of the lens or optic usable for forming the conjugate image of an object or for focusing light from a distant point source to a single focus, or to a plurality of predetermined foci in the case of a multifocal optic or lens. It will be appreciated that the term clear aperture does not limit the transmittance of the lens or optic to be at or near 100%, but also includes lenses or optics having a lower transmittance at particular wavelengths or bands of wavelengths at or near the visible range of the electromagnetic radiation spectrum. In some embodiments, the clear aperture has the same or substantially the same diameter as the optic. Alternatively, the diameter of the clear aperture may be smaller than the diameter of the optic, for example, due to the presence of a glare or PCO reducing structure disposed about a peripheral region of the optic.

The anterior surface 104 has an anterior shape or base curvature 114 and the opposing posterior surface 106 has a posterior shape or base curvature 116, the shapes 114, 116 providing a refractive power that is generally sufficient to at least provide distant vision. The optic 102 may further comprise a multifocal pattern 118 that is added to the anterior shape 114, the multifocal pattern 118 being configured to provide two or more foci within the visible range of the electromagnetic spectrum, for example, a focus selected to provide distant vision and a focus selected to provide near vision to a subject, or a focus selected to provide distant vision and a focus selected to provide intermediate vision to a subject.

As used herein, the term "near vision" means vision produced by an eye that allows a subject to focus on objects that are within a range of about 25 cm to about 40 cm from the subject, or at a distance at which the subject would generally place printed material for the purpose of reading. As used herein, the term "intermediate vision" means vision produced by an eye that allows a subject to focus on objects that are located from about 40 cm to about 2 meters from the subject. As used herein, the term "distant vision" means vision produced by an eye that allows a subject to focus on objects that are at a distance that is greater than 2 meters, at a distance of 5 meters or about 5 meters from the subject, or at a distance of 6 meters or about 6 meters from the subject. The object distance may also be expressed in relation to an amount of add power, in Diopters, suitable for focusing an object at that distance onto the retina of an emmetropic eye. For example, an add power of 1 Diopter is suitable for focusing an object onto the retina that is located at a distance of 1 meter from an emmetropic eye in a disaccommodative state (e.g., with a relaxed ciliary muscle), while add powers of 0.5 Diopter, 2 Diopters, 3 Diopters, and 4 Diopters are suitable for focusing an object onto the retina that is located at a distance of 2 meters, 50 cm, 33 cm, and 25 cm, respectively, from an emmetropic eye in a disaccommodative state.

The shapes 114, 116 of the optic 102 may have a shape or profile that may be either spherical or aspheric. The shape of the surface may be represented by sag Z given by the following equation:

$$Z(r) = \frac{r^2/R}{1+\sqrt{1-r^2(CC+1)/R^2}} + ADr^4 + AEr^6 + \ldots$$

where r is a radial distance from the center or optical axis of the lens, R is the curvature at the center of the lens, CC is the so-called conic constant, and AD and AE are polynomial coefficients additional to the conic constant CC. While the optic 102 is biconvex in the illustrated embodiment, other lens shapes are a possible, for example, plano-convex, plano-concave, bi-concave, and the like.

The optic 102 further comprises an extended focus pattern or mask 120 that is disposed on, added to, or combined with the posterior shape 116, the extended focus pattern 120 being configured to provide an extended depth of focus. The extended focus mask 120 is configured to extend the depth of focus of the at least one of the foci produced or provided by the multifocal pattern 118. For example, the optic 102 may be a bifocal optic providing two foci or optical powers within the visible light band. In such embodiments, the first and second foci of the optic 102 each have a depth of focus that is greater than the depth of focus for each of the foci of a multifocal reference optic without the mask 120, the reference optic having a base power, an add power, and a clear aperture that are equal or substantially equal to that of the intraocular lens 100 or the optic 102.

As used herein, the terms "extended focus" or "extended depth of focus," mean a depth of focus of a test lens, optic, or optical element (generally referred to herein as an "optic") that exceeds the depth of focus of a reference optic comprising biconvex or biconcave surfaces of equal radii of curvature, the reference optic having an optical power or focal length that is equal to an optical power or focal length of the test optic, wherein the depth of focus for the test optic and the reference optic are determined under the same aperture conditions and under equivalent illumination conditions (e.g., the same or an equivalent object, such as a point light source or a test target, for each optic that is placed the same distance or distances from each optic). In the case of a multifocal test optic, the reference optic may comprise a monofocal optic having a focal length or optical power that is equal to one of optical power or focal length of the test optic. In the case where the extended focus or extended depth of focus is attributable to a particular feature, structure, or mask associated with the test optic, the reference optic may be one that is made of the same material and has the same structure as the test optic, except without the particular feature, structure, or mask. For example, if a test optic is a refractive or diffractive multifocal optic comprising a mask for extending the focus or depth of focus of at least one of the foci formed by the test optic, then a suitable reference optic may be one made of the same material(s) as the test optic having the same structure as the test optic (e.g., surface shapes/curvatures, thickness, aperture, echelette geometry, and the like), except without the mask.

As used herein, the terms "optical power" of an intraocular lens or associated optic means the ability of the intraocular lens or optic to focus light when disposed within a media having a refractive index of about 1.336 (the average refractive index of the aqueous and vitreous humors of the human eye; see ISO 11979-2). As used herein the terms "focus" or "focal length" of an intraocular lens or associated optic is the reciprocal of the optical power in meters when the intraocular lens is disposed within a media having a refractive index of 1.336. As used herein the term "power" means "optical power". As used herein, the term "light" means incident electromagnetic radiation within the visible waveband, for example, electromagnetic radiation with a wavelength in a vacuum that is between 390 nanometers and 780 nanometers. Except where noted otherwise, optical power (either absolute or add power) of an intraocular lens or associated optic is from a reference plane through the intraocular lens or associated optic (e.g., a principal plane of an optic).

As used herein, the term "depth of focus" generally refers to a range of placement of an image plane over which an image produced by an optic or lens system (e.g., the cornea and an intraocular lens) maintains a predetermined optical performance, and generally refers to an image-side depth or range. The depth of focus may be determined, for example, by moving an object (e.g., a resolution target or a point light source) along an optical axis and determining the range of corresponding images that maintain a predetermined optical performance at the image plane. It will be appreciated that the depth of focus may be alternatively expressed in terms of "depth of field", which generally refers to a range object locations over which a corresponding image produced by an optic or lens system maintains a predetermined optical performance at an image plane, and generally refers to an object-side depth or range. The predetermined optical performance for determining either depth of focus or depth of field may be based on various criteria, such as through-focus performance or variation (either absolute or percent, such as full-width-half-max (FWHM)) of MTF, spot size, wavefront error, Strehl Ratio, or any other suitable criterion or performance metric.

In determining or providing a depth of focus, an extended focus, or an extended depth of focus, the determination may be based on through-focus MTF data at a particular spatial frequency. For example, the depth of focus may be defined as the region in a through-focus plot over which the Modulation Transfer Function (MTF) at a spatial frequency of 50 line pairs per mm exceeded a selected cutoff value. Typical cutoff values may include 0.05, 0.10, 0.15, 0.17, 0.20, 0.25, or higher. Other spatial frequencies may include 25 line pairs per mm or 100 line pairs per mm. Another way to define the depth of focus is based on a relative threshold, where the threshold is defined based on a peak value of a figure of merit. For instance, the depth of focus may be defined as the full width at half max (FWHM) of the MTF at a particular spatial frequency. Other relative thresholds may be 95%, 90%, 80%, 70%, 60%, 50%, 1/e, 1/e^2 of a peak value of the MTF, or any suitable fraction of the peak value of MTF or another metric.

The depth of focus may be defined in terms of an axial distance, or, equivalently, in terms of a power. The figures of merit, or metrics, may be either purely optical in nature, or may incorporate some perception effects from the human eye. For instance, any or all of the following optical metrics may be used: MTF at a particular spatial frequency, MTF volume (integrated over a particular range of spatial frequencies, either in one dimension or in two dimensions), Strehl ratio, encircled energy, RMS spot size, peak-to-valley spot size, RMS wavefront error, peak-to-valley wavefront error, and edge transition width.

Alternatively, any of the following psychophysical metrics may be used: contrast sensitivity, visual acuity, and perceived blur. In addition, other metrics may be found in the literature, such as those detailed in Marsack, J. D., Thibos, L. N. and Applegate, R. A., 2004, "Metrics of optical quality derived from wave aberrations predict visual performance," J Vis, 4 (4), 322-8; Villegas, E. A., Gonzalez, C., Bourdoncle, B., Bonnin, T. and Artal, P., 2002, "Correlation between optical and psychophysical parameters as a function of defocus," Optom Vis Sci, 79 (1), 60-7; van Meeteren, A., "Calculations on the optical transfer function of the human eye for white light," Optica Acta, 21 (5), 395-412 (1974), all of these references being herein incorporated by reference in their entirety.

Any or all of the above metrics may be defined at a single wavelength, such as 550 nm or any other suitable wavelength, at a plurality of selected wavelengths, or over a spectral region, such as the visible spectrum from 400 nm to 700 nm. The metrics may be weighted over a particular spectral region, such as the weighting associated with the spectral response of the human eye. It will be appreciated that the above criteria may be used in determining or comparing the performance of any of the optic discussed herein.

In certain embodiments, a test optic with an extended depth of focus may be evaluated in terms of its optical performance over a range of defocus conditions, as compared to a reference optic (e.g., as defined above herein). For example, the test optic with an extended depth of focus may have an MTF that is above a predetermined threshold value (e.g., 0.05, 0.10, 0.15, 0.17, 0.20, 0.25, or higher) at a particular frequency (e.g., 25, 50, or 100 line pairs per mm) over a defocus range that is greater than that of the corresponding reference optic. The defocus range may be expressed in terms of object space distances, image space distances, or Diopter power. In some embodiments, the test optic with an extended depth of focus may specified in terms of an increased in depth of focus as compared to the corresponding reference optic, either in absolute terms (e.g., an increased defocus range compared to the reference optic over which a predetermined MTF performance is maintained) or in relative terms (e.g., a percent increase in defocus range compared to a reference optic, such as a 10%, 20%, 50%, 100%, 200%, or greater increase in defocus range compared to a reference optic).

Referring to FIG. 4, which is a front view of the optic 102 only and without the haptics 110, the multifocal pattern 118 comprises a plurality of echelettes including a central echelette that is generally circular and surrounded by a plurality of annular echelettes. The outer diameter and surface shape of each echelette are generally selected to provide constructive interference between the echelettes when light is incident on the optic 102, wherein light in two or more diffractive orders of the multifocal pattern 118 are focused to different points or foci along the optical axis OA. In some embodiments, the multifocal pattern 118 comprises a refractive multifocal element, for example, having radial profile as disclosed in U.S. Pat. No. 5,225,858 (Lang) or U.S. Pat. No. 6,210,005 (Portney), which are herein incorporated in their entirety. Typically, the multifocal pattern 118 has an add power of at least 2 Diopters, 3 Diopters, or 4 Diopters, depending on such factors as patient or doctor preference, accommodative capabilities of the intraocular lens 100 and/or eye 10, and the nature of the extended focus mask 120.

Figure 5:
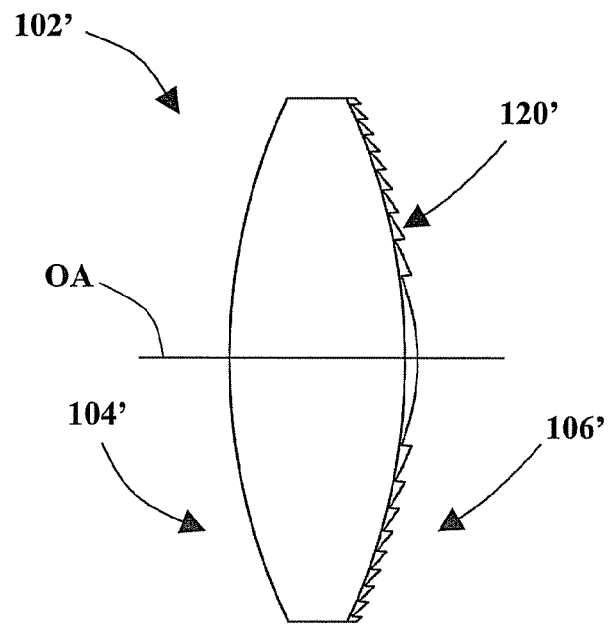
FIG. 5 is a side view of an optic showing a low-add diffractive mask according to an embodiment of the present invention.

Referring to FIG. 5, an exemplary extended focus mask is illustrated for an optic 102' comprising an anterior surface 104' and a posterior surface 106' disposed about an optical axis OA. The extended focus mask of the optic 102' is in the form of a low-add diffractive mask 120' disposed on, added to, or combined with a base curvature or shape of the posterior surface 106'. The low-add diffractive mask 120' may comprise a blazed profile, for example, as described by equations equal or similar to those in an article by A. L. Cohen, "Practical design of a bifocal hologram contact lens or intraocular lens," Applied Optics, 31(19), 3750-3754 (1992). The diffractive element provided two foci corresponding to the $0^{th}$ and $+1^{st}$ diffracted orders of the low-add diffractive mask 120'.

The radius of a first central echelette from an optical axis may be 0.95 mm, corresponding to an add power of about 1.2 Diopters for a silicone lens disposed within aqueous humor of the human eye. The depth of the profile is 3.2 microns, which converts to a phase imparted upon transmission of (3.2 microns times (1.459-1.336) divided by design wavelength of 0.555 microns, where 1.336 is the refractive index of the aqueous humor), or about 0.7 wavelengths, or about 255 degrees of phase. The parabolic profile extends across all zones, with a step discontinuity at the edge of each zone.

To assess the ability of the low-add diffractive mask 120' to produce an extended depth of focus, an eye model was used in which the optic 102' was configured for use as an intraocular lens. The optic 102' was modeled as a biconvex lens in which the surfaces 104', 106' each had a base radius of curvature of 12.154 mm with a conic constant of 0 (i.e., spherical surfaces). In other words, the shape of the anterior and posterior surfaces were spherical. Alternatively, the anterior and/or posterior surfaces of the lens may include a non-zero conic constant or one or more aspheric terms. The lens material was a silicone material with a refractive index of about 1.459 at a wavelength of 555 nm. The thickness between the surfaces 104', 106' along the optical axis OA was selected as 1 mm.

The optic 102' was modeled as an intraocular lens and placed into an eye model under polychromatic light conditions, as described in an article by H. L. Liou. and N. A. Brennan, "Anatomically accurate, finite model eye for optical modeling," J Opt Soc Am A, 14(8), 1684-1695. The Liou-Brennan model eye uses distances and curvatures that correspond to those in an average-shaped, average-sized human eye.

The model used an object placed at infinite distance from the eye. The media between the object and the eye was air with a refractive index of 1. The model included a model cornea with a radius of curvature of +7.77 mm and a conic constant (also known as "asphericity") of −0.18. The model cornea had a thickness of 0.5 mm and a refractive index of about 1.376 at a wavelength of 555 nm. The posterior surface of the cornea had a radius of curvature of +6.4 mm and a conic constant of −0.6. The eye model also included an iris located a distance of 3.16 mm from the cornea posterior surface along the optical axis OA.

The optic 102' was disposed along an intraocular lens plane located 0.5 mm from iris. The refractive index of the material between the cornea posterior surface and the optic 102' was that of the aqueous humor, which is equal to 1.336 at a wavelength of 555 nm. The separation between posterior surface 106' and the iris (image plane) was about 18.7 mm; however, the value was set as a "solve" value, for example as used in raytrace programs such as OSLO or ZEMAX. The refractive index between the optic 102' and the retina was set to that of the vitreous humor, 1.336 at a wavelength of 555 nm.

A reference optic was also modeled as a benchmark for comparison to the optic 102' using the Liou-Brennan model eye as specified above. The reference optic had a base power and a clear aperture that are substantially equal to that of the optic 102'. Like the optic 102', the reference optic also was modeled as a biconvex lens with anterior and posterior surfaces with a radius of curvature of 12.154 mm with a conic constant of 0 (i.e., spherical surfaces). Also like the optic 102', the anterior/posterior surfaces were separated by 1 mm along the optical axis.

A simulation based on the above model eye was performed in order to evaluate the optical performance of the optic 102'. The eye model was also used to compare the performance of the optic 102' to the reference optic described in the previous paragraph. Additionally or alternatively, the eye model may be used to adjust the design of the optic 102' by modifying certain parameters of the optic 102' so as to provide a predetermined optical performance, an optimized optical performance based on a metric, and/or an improved optical performance compared to a reference optic. For example, the amount of add power may be adjusted to provide a design of the optic 102' that provides a desired performance.

The simulation based on the above model eye used a primary wavelength of 555 nm and a weighting for other wavelengths in accordance with the spectral response of the eye. In other embodiments, the optic 102' may be designed and/or evaluated using other weighting factors, for example, to account for varying lighting conditions and/or to account for differences between scotopic and photopic vision. Alternatively, the optic 102' may be designed and/or evaluated at a plurality of two or three wavelengths representative of the visible range or a particular lighting condition, or at a single wavelength representative of the visible range or a particular lighting condition (e.g., at a wavelength of 550 nm).

Figure 6:
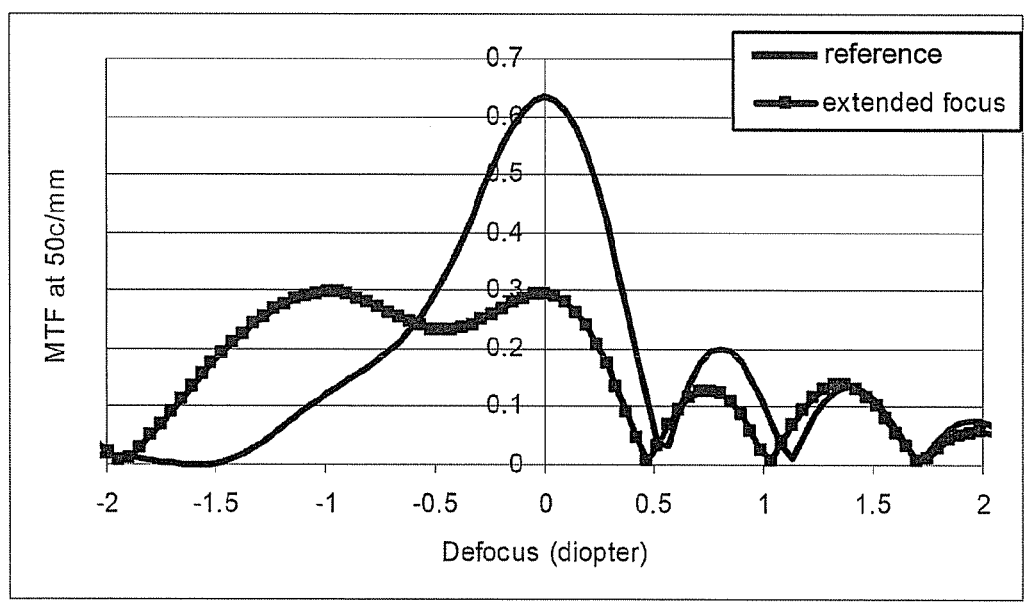
FIG. 6 is a through-focus plot of a simulated Modulation Transfer Function for the optic shown in FIG. 5

FIG. 6 is a through-focus plot of the simulated Modulation Transfer Function at 50 line pairs per mm (or, equivalently, cycles per mm or c/mm) for the optic 102' containing the low-add diffractive mask 120' and the reference optic w/o a low-add diffractive mask. The plots show the performance of the optic 102' and the reference optic when each is placed in the eye model. The extended focus optic 102' has a reduced peak MTF, but an increased width to the MTF curve, compared to the reference optic.

A depth of focus for the two optics based on the results shown in FIG. 6 may be defined in various ways. One definition of depth of focus is the continuous range over which the MTF is above a threshold value of 0.17, for example. Using this definition, the reference optic has a depth of focus of 1.36 Diopters, and the optic 102' has a depth of focus of 1.90 Diopters, which is about 39% larger than the reference optic. Another definition of depth of focus uses a threshold value of 0.20, for example. Using this definition, the reference optic has a depth of focus of 1.25 Diopters and the optic 102' has a depth of focus of 1.72 Diopters, which is about 37% larger than the reference optic. It will be appreciated that such definitions may be used to evaluate the depth of focus and/or performance for any lens or optic according to embodiments of the present invention.

Returning to the illustrated embodiment of FIGS. 2-4, the extended focus mask 120 of the multifocal optic 102 comprises a diffractive pattern providing a low add power that is similar or equivalent to the low-add diffractive mask 120' discussed above. The mask 120 comprises a diffractive pattern that is generally similar to the multifocal pattern 118 in that the mask 120 includes a plurality echelettes configured to provide constructive interference. However, in contrast to the multifocal pattern 118, the mask 120 is constructed to provide a relatively low add power, for example, less that 2 Diopters, less than 1.5 Diopter, or even less than 1 Diopter of add power. The relatively low add power provided by the mask 120 serves to extend the depth of focus of at least one of the two foci of the optic 102 produced by the multifocal pattern 118 in cooperation with the refractive surfaces 114, 116.

Surprisingly, the low-add power of the extended focus mask 120 not only extends the depth of focus of the individual foci produced by the multifocal pattern 118, but may be configured to also provide enhanced visual acuity or performance over a range of viewing distances between the two view distances corresponding to the two foci of the multifocal pattern 118 (e.g., having an MTF at 50 line pairs per mm or 100 line pairs per mm that is above 0.05, 0.10, 0.15, 0.17, 0.20, or more). For example, the multifocal pattern 118 may be selected to produce a first focus corresponding to distant vision (e.g., in which objects at distances of at least 6 meters, or at 10 meters or farther, appear to be in focus) and a second focus corresponding to near vision (e.g., in which objects at 30 cm, 35 cm, or less than 40 cm appear to be in focus). In such embodiments, the extended focus mask 120 may be configured to increase visual acuity or optical performance not only at distances near the foci of the multifocal pattern 118 (e.g., at distances of 25 cm, 40 cm, and/or 6 meters), but also over a range of distances therebetween (e.g., at distances of 1 meter, 2 meters, 3 meters, 4 meters, and/or 5 meters).

In certain embodiments, one of the focal lengths of the optic 102 and/or the multifocal pattern 118 corresponds to a predetermined viewing distance for intermediate vision, or to a predetermined viewing distance that is between intermediate vision and distant vision (e.g., a predetermined viewing distance that is from about 2 meters to about 6 meters). In such embodiments, the optic 102 and the extended focus mask are configured so that the visual acuity or performance of the optic 102 is above a threshold value both for distant vision, the predetermined viewing distance, and viewing distances that are less than the predetermined viewing distance (e.g., having an MTF at 50 line pairs per mm or 100 line pairs per mm that is above 0.05, 0.10, 0.15, 0.17, 0.20, or more). For example if the predetermined viewing distance is selected to be 5 meters, the optic 102 may be configured to provide a predetermined visual acuity or optical performance at distances of 4 meters, 5 meters, 6 meters, and at distances greater than 6 meters.

In certain embodiments, one of the foci of the optic 102 and/or the multifocal pattern 118 is selected to correspond to a so-called "hyperfocal distance," and the visual acuity or performance of the optic 102 is above a threshold value for objects at distances that are greater than the hyperfocal distance and for objects at distances that are less than the hyperfocal distance (e.g., having an MTF at 50 line pairs per mm or 100 line pairs per mm that is above 0.05, 0.10, 0.15, 0.17, 0.20, or more). As used herein, the term "hyperfocal distance" means a distance from a healthy, emmetropic eye, at which an add power of 0.5 Diopters in the spectacle plane provides visual acuity at least 20/20, based on the standard Snellen test for visual acuity. For example, in a human eye with an axial length (AL) of 25 mm, the hyperfocal distance is approximately 2.5 meters from the eye. As used herein, the term "emmetropic eye" means an eye having a visual acuity for distant vision of at least 20/20, based on the standard Snellen test for visual acuity. As used herein, the term "emmetropic vision" means vision which provides a visual acuity for distant object of at least 20/20. In such embodiments, the optic 102 may be configured to provide a predetermined visual acuity or optical performance at distances of 1 meter or 1.5 meters, at a distance of 2.5 meters, and at a distance greater than 2.5 meters (e.g., 3 meters, 4 meters, 6 meters, and/or distances greater than 6 meters).

In other embodiments, a first focal length of the optic 102 and/or the multifocal pattern 118 is set to correspond to a first distance that is greater than that typical for near vision, while a second focal length of the optic 102 and/or the multifocal pattern 118 is set to correspond to distant vision or a relatively large viewing distance such as a hyperfocal distance or some other distance between about 3 meters and 6 meters. For example, the first focal length may be selected to correspond to a distance of or about 40 cm, 50 cm, 1 meter, or 1.5 meters, while the second focal length corresponds to a distance of or about 2.5 meters, 3 meters, 4 meters, or 5 meters. In such embodiments, the optic 102 may provide visual acuity that is above a predetermined threshold over all distances between the distances corresponding to the first and second focal lengths (e.g., having an MTF at 50 line pairs per mm or 100 line pairs per mm that is above 0.05, 0.10, 0.15, 0.17, or 0.20 at all distances between 50 cm and 2.5 meters or between 50 cm and 3 meters). In such embodiments, the extended depth of focus of the two foci produced by the combination of the multifocal pattern 118, the extended focus mask 120, and the refractive power of the surfaces 104, 106 may be configured to provide functional vision and/or a contrast sensitivity that is above a predetermined threshold over an entire range of distances (e.g., a predetermined vision performance for objects disposed anywhere between 14 inches and 20 feet from a subject). For example, a multifocal lens having a near (or intermediate) focus point and a distance focus point may be configured so that the through-focus MTF of the intraocular lens within an eye model or subject eye is above a predetermined threshold value for all add powers between zero and 3 Diopters or between zero and 4 Diopter.

It will be appreciated that structural and material variations of the optic 102 as compared to the illustrated embodiment of FIGS. 2-4 are include herein. For example, the extended focus mask 120 may be disposed on the anterior surface 104, while the multifocal pattern 118 may be disposed on the posterior surface 106. Alternatively, the multifocal pattern 118 and the mask 120 may be combined onto a single surface 104 or 106. Furthermore, the multifocal pattern 118 may be replaced with or supplemented by a refractive multifocal pattern. Also, the extended low-add diffractive mask 120 illustrated in FIGS. 2-4 may be replaced by or combined with another type of pattern or mask that is selected to provide an extended depth of focus to one or more of the foci produced by the multifocal pattern 118. In certain embodiments, at least one of the surfaces 104, 106 comprises a diffractive pattern that is apodized or is otherwise configured to provide an optical performance and/or depth of focus that varies with a subject's pupil size or varying light conditions, for example, as discussed by Lee et al. in U.S. Pat. No. 5,699,142. In addition, structural and/or material characteristics of the optic 102 may be configured to reduce, compensate for, or eliminate aberrations produced by the optic itself, the cornea, the eye, or the combination of the optic with the cornea or eye. For example, at least one of the surfaces of the optic 102 may be aspheric and configured to reduce, compensate for, or eliminate a spherical aberration (e.g., have an negative spherical aberration that reduces, compensates for, or eliminates a positive spherical aberration of a cornea or eye). Additionally or alternatively, the materials and/or a diffraction grating on one or both surfaces of the optic 102 may be selected to reduce, compensate for, or eliminate chromatic aberration (e.g., produced by the optic itself, the cornea, the eye, or the combination of the optic with the cornea or eye).

Referring to FIGS. 7-9, in certain embodiments, an intraocular lens 200 comprises an optic 202 including an extended focus mask that is in the form of a phase-affecting, non-diffractive mask 220. Examples of such non-diffractive masks are disclosed by Zalevsky in U.S. Pat. No. 7,061,693, which is herein incorporated by reference in its entirety. The optic 202 has a clear aperture 212 that is disposed about a central axis or optical axis OA. The optic 202 includes an anterior surface 204 having an anterior shape or base curvature 214 and an opposing posterior surface 206 having a posterior shape or base curvature 216. The non-diffractive mask 220 is disposed on, added to, or combined with the posterior shape 216 so as to increase a depth of focus of at least one focus of the optic 202. The optic 202 may include a multifocal element or pattern 218 that is disposed on, added to, or combined with the posterior shape 216. The first and second surfaces 204, 206 together provide a base power and an add power.

The phase-affecting, non-diffractive mask is configured in accordance with the parameters of the optic 202, i.e., its effective aperture and optionally also the optical power distribution and/or focal length. The mask 220 may be implemented integral with the optic 202, for example, as a pattern on the lens surface. Alternatively, the mask 220 may be a separate element attached to the optic 202 or located close thereto. Generally, the mask 220 is configured as a phase-only binary mask; however, the mask 220 may be configured as a phase and amplitude mask.

The mask 220 may be configured to define at least one spatially low frequency transition region, and the mask 220, together with the optic 202, define a predetermined pattern of spaced-apart optically or substantially optically transparent features differently affecting the phase of light passing therethrough. The pattern of the mask 220 is thus formed by one or more transition regions along the posterior surface 206. The transition regions are π-phase transitions for a certain wavelength for which the mask 220 is designed. The arrangement of these transition regions (positions within the posterior surface 206) is determined by the effective aperture of the given imaging optic 202 (and possibly also optical power of the lens) so as to increase a defocused Optical Transfer Function (OTF) of the intraocular lens 200. To this end, the pattern of the mask 220 may be configured to generate a desired phase interference relation between light portions passing through different regions of the optic 202.

The mask 220 may be implemented as a surface relief on the imaging lens, as illustrated in FIG. 8. Alternately, the mask 220 may be implemented as a pattern of regions made of a second material than that of the optic 202 base material. The second material is generally transparent or substantially transparent, and may have a refractive index that is different from that of the optic 202. The second material may be disposed on selective spaced-apart regions of the surface 206. Alternatively, the pattern may be machined or molded into the surface 206.

Figure 10:
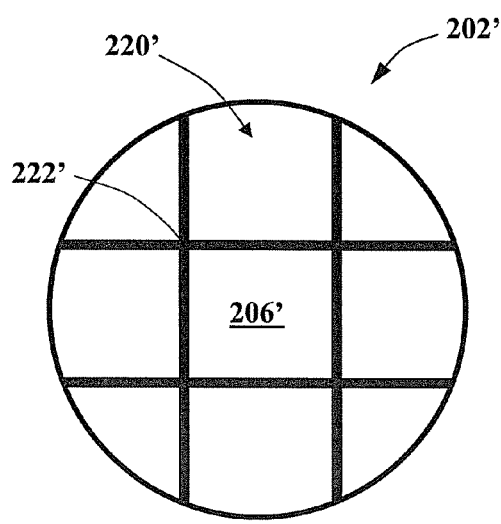
FIG. 10 is a front view of a phase-affecting, non-diffractive mask according to another embodiment of the present invention.
Figure 11:
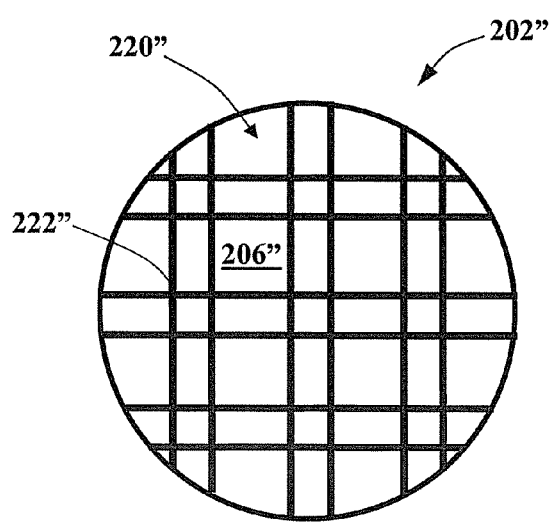
FIG. 11 is a front view of a phase-affecting, non-diffractive mask according to yet another embodiment of the present invention.

In the illustrated embodiment, the non-diffractive mask 220 comprises an annular transition region 222. It will be appreciated that other configurations of one or more transition regions may be additionally or alternatively used. For example, referring to FIGS. 10 and 11, masks 220' and 220" comprise linear transition regions 222' and 222". In the example of FIG. 10, the mask 220 comprises a grid formed by two mutually perpendicular pairs of bars. In the example of FIG. 11, the mask 220 comprises a mask formed by a two-dimensional array of basic grid-elements. For example, the transition regions along the bar line may be π-phase transitions and the regions of intersection between the bars may be zero-phase transitions. Other patterns are anticipated, for example, combinations of linear, circular, and/or arcuate pattern elements. The pattern of the mask 220 may and may not be symmetrical relative to the center of the lens. For example, the four π-phase bars, two vertical (along Y-axis) and two horizontal (along X-axis) bars, that are illustrated in FIG. 10, may be shifted transversally along the x-y plane to be not centered around the center of the lens. The pattern of the mask 220 may be configured to define microstructures inside the phase transition region (e.g., inside the π-phase transition ring of FIG. 9), namely, each phase transition region may be of a variable spatially low frequency of phase transition such as for example π/2, π, and so forth.

In certain embodiments, an improved or optimized mask 220 contour for the optic 202 is obtained by a solving algorithm, for example as is described by Zalevsky in U.S. Pat. No. 7,061,693. In such embodiments, the mask 220 may be designed to increase or maximize a defocused OTF of an ocular imaging system, by generating invariance to quadratic phase factor (which factor is generated when the image is defocused and multiplies the CTF of the imaging lens).

The optic 202 and the non-diffractive mask 220 may incorporate, where appropriate, any of the elements discussed above with regard to the optics 102, 102' or the masks 120, 120'.

In certain embodiments, an optic comprises an extended focus pattern or mask comprising a surface profile like those taught in U.S. Pat. No. 6,126,286 (Portney), U.S. Pat. No. 6,923,539 (Simpson et al.), U.S. Pat. No. 7,287,852 (Fiala), or U.S. Pat. No. 7,293,873 (Dai)., or U.S. Patent Application Number 2006/0116763 (Simpson), all of which are herein incorporated by reference. Such devices and means of extending depth of focus may replace or supplement those already discussed above herein (e.g., replacing or supplementing masks 102, 102', 202). For example, a pattern of surface deviations may be superimposed on at least one of the base curvatures or shapes 114, 116 of the optic 102, so as to modulate the topography of at least one of the surfaces 104, 106 in a range of about −0.5 microns to about +0.5, as disclosed in U.S. Pat. No. 6,923,539.

Figure 12:
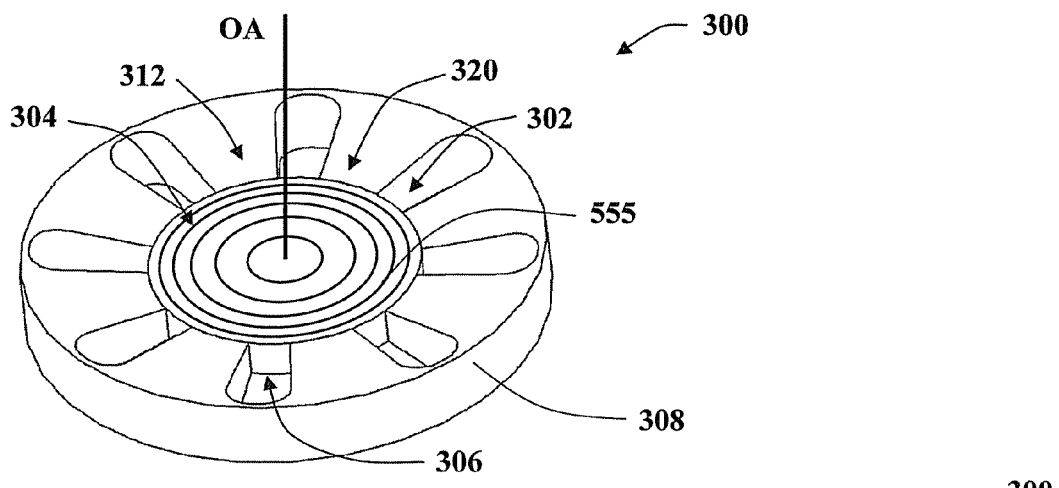
FIG. 12 is a perspective view of an accommodating intraocular lens according to an embodiment of the present invention.
Figure 13:
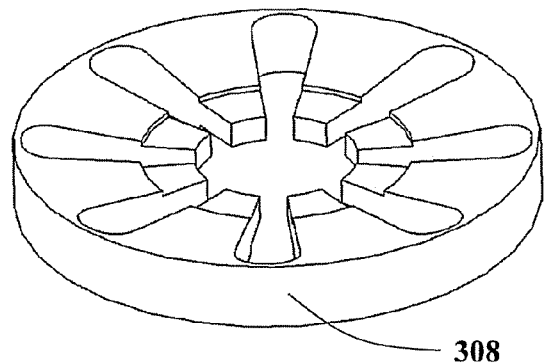
FIG. 13 is a perspective view of a positioning member the accommodating intraocular lens shown in FIG. 12.
Figure 14:
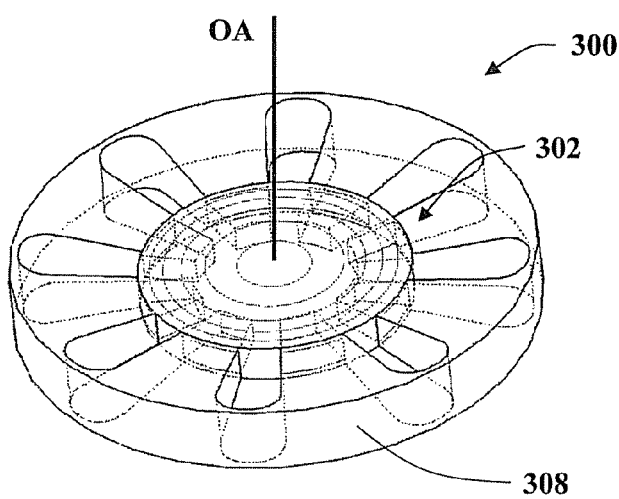
FIG. 14 is a perspective view of the accommodating intraocular lens shown in FIG. 12 showing arms from the positioning member protruding into an optic.

Referring to FIGS. 12-14, an accommodating intraocular lens 300 comprises an optic 302 having a clear aperture 312 disposed about an optical axis OA, the optic including an anterior surface 304 and a posterior surface 306. The intraocular lens 300 also comprises a positioning member 308, wherein the positioning member 308 is generally configured to provide accommodative action by transferring an ocular force to the optic 302. In the illustrated embodiment, the ocular force deforms the optic 302 which is preferably made of a relatively soft material, for example, having a modulus of elasticity of less than 200 kPa, 100 kPa, or 50 kPa. The optic thereby changes shape and optical power in response to the ocular force, for example, by changing the radius of curvature of at least one of the surfaces 304, 306. Alternatively or additionally, the intraocular lens 300 may be configured to provide accommodative action by moving the optic 302 along the axis OA in response to an ocular force, especially in relation to one or more other stationary or moving optics.

The optic 302 comprises an extended focus pattern or mask 320 that is disposed on, added to, or combined with a base curvature or shape of the anterior surface 304, the extended focus mask 320 being configured to provide an extended depth of focus for a focus of the optic 300. The intraocular lens 300 has a depth of focus, when illuminated by a light source over the entire clear aperture, that is greater than a depth of focus of a reference optic without the mask, the reference optic having a base power, an add power, and a clear aperture that are equal or substantially equal to that of the intraocular lens 300.

The ocular force to the intraocular lens 300 may be provided directly by the capsular bag into which the intraocular lens 300 is place. Alternatively, the positioning member 308 may be configured so that the ocular force used to deform the optic 302 is provided more directly by the ciliary muscle and/or the zonules, for example, by removing the capsular bag or placing the intraocular lens 300 in front of the capsular bag. In any case, the intraocular lens 300 is generally configured to provide a predetermined amount of accommodation when the ciliary muscle contracts and/or relaxes and with an ocular force of less than 20 grams force, less than 10 grams force, or even less than 5 grams force.

The intraocular lens 300 is configured to have a predetermined ocular power when in a reference state, for example, in which no or substantially no external forces on the intraocular lens 300 expect for that of gravity. In some embodiments, while there is no or substantially no external force on the intraocular lens 300 when in the reference state, the intraocular lens 300 may experience internal forces, for example, produced between the optic 302 and the positioning member 308 due to a pre-stress introduced during fabrication. The optical power of the intraocular lens 300 when in the reference state may be selected to provide near vision (an accommodative bias), distant vision (a disaccommodative bias), or intermediate vision.

It will be appreciated that variations of the structure illustrated in FIGS. 12-14 may be used. For example, the extended focus mask 320 may be disposed on the posterior surface 306. Additionally, at least one of the surfaces 304, 306 may incorporate a multifocal profile (diffractive or refractive) on the same or opposite surface containing the mask 320. In general, the optic 302 and the mask 320 may incorporate, where appropriate, any of the elements discussed above with regard to the optics 102, 102', 202 or the masks 120, 120', 220. For example, at least one of the surfaces of the optic 302 may comprise a diffractive or refractive multifocal profile or mask with a maximum add power of at least 1.5 Diopters or 2.0 Diopters, for example to enhance or compensate for a sufficient ocular force to provide a desired amount of accommodative axial movement and/or deformation.

The extended focus mask 320 in the illustrated embodiment comprises a diffraction mask similar or equivalent to the extended focus pattern or mask 120 or the low-add diffractive mask 120'. However, the mask 320 in the illustrated embodiment may be replaced or combined with any profile or mask suitable for providing an extended depth of focus, for example, like the phase-affecting, non-diffractive mask 220 or of one or more of the designs disclosed in the prior art publication cited above herein.

Embodiments of the present invention may also be incorporated to extend or enhance the depth of focus of various prior art accommodating intraocular lens that use a deformable optic and/or axial travel, such as those disclosed in U.S. Pat. No. 7,048,760 (Cumming), U.S. Pat. No. 6,846,326 (Zadno-Azizi et al.), or U.S. Pat. No. 6,488,708 (Sarfarazi), or U.S. Patent Application Publication Number 2004/0111153 (Woods et al.) or 2007/0129803 (Cumming et al.), or U.S. patent application Ser. No. 11/618,325 (Brady et al.), or Ser. No. 11/618,411 (Brady et al.), all of which are herein incorporated by reference in their entirety. The intraocular lens 300 is generally configured to change the optical power of the optic 302 by at least about one Diopter, preferably by at least 2 Diopter, 3 Diopter, or 4 Diopters.

For example, in certain embodiments, an accommodating intraocular lens comprises a single flexible optic having anterior and posterior sides, similar to that disclosed in U.S. Pat. No. 7,048,760. In such embodiments, the intraocular lens may further comprise at least two portions extending from the optic, the portions having hinged inner ends adjacent the optic and outer ends distal to the optic, the outer ends being movable anteriorly and posteriorly relative to the optic, and the portions having at least one flexible fixation finger at the outer ends of the portions.

In certain embodiments, an accommodating intraocular lens is configured to fill the capsular bag, for example, as disclosed in U.S. Patent Application Publication Number 2004/0111153, or U.S. patent application Ser. Nos. 11/618, 325 or 11/618,411. In such embodiments, the accommodating intraocular lens may comprise a positioning member including opposing anterior and posterior arcuate segments and a plurality of circumferentially spaced legs each having a first end joined to the optic and a second end joined to at least one of the arcuate segments. In other embodiments, an accommodating intraocular lens comprises two or more separate optical elements, for example, as disclosed in U.S. Pat. Nos. 6,846,326 or 6,488,708. Such a configuration may beneficially provide a relatively large amount of accommodation with a relatively small amount of axial motion between the two separate optical elements.

The description of the invention and its applications as set forth herein is illustrative and is not intended to limit the scope of the invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

What is claimed is:

1. An intraocular lens, comprising:
   an optic having an aperture disposed about an optical axis; and
   a positioning member coupled to the optic;
   the optic comprising:
   a first surface and an opposing second surface;
   a diffractive multifocal profile disposed on the first surface or the second surface, wherein the diffractive multifocal profile provides a base power and an add power; and
   an extended focus mask disposed on at least one of the surfaces, wherein the extended focus mask comprises a diffractive pattern having an add power that is less than or equal to about 1.5 Diopters and wherein the extended focus mask is configured to extend the depth of focus of the base power, the add power, and a range of viewing distances between the base power and the add power.

2. The intraocular lens of claim 1, wherein the apertures are clear apertures of the optics.

3. The intraocular lens of claim 1, wherein the apertures are circular and have a diameter of at least 4.5 mm.

4. The intraocular lens of claim 1, wherein at least one of the first and second surfaces includes at least one of a spherical aberration and a chromatic aberration, the at least one aberration selected to correct at least one of a spherical aberration and a chromatic aberration of the eye.

5. The intraocular lens of claim 4, wherein the spherical aberration is a negative spherical aberration that is selected to a at least partially compensate for a positive spherical aberration of a cornea the eye.

6. The intraocular lens of claim 1, wherein the optic comprises opposing convex spherical surfaces with common base curvatures.

7. The intraocular lens of claim 1, wherein the positioning member comprises opposing anterior and posterior arcuate segments and a plurality of circumferentially spaced legs each having a first end joined to the optic and a second end joined to at least one of the arcuate segments.

8. The intraocular lens of claim 1, wherein the ocular force is less than 20 grams force.

9. The intraocular lens of claim 1, the intraocular lens configured to change the optical power of the base power of the intraocular lens by at least 1 Diopter.

10. The intraocular lens of claim 9, wherein the positioning member includes a plurality of radial segments that are shaped to conform to an equatorial region of the capsular bag.

11. The intraocular lens of claim 1, wherein the intraocular lens is optically described by a model lens, such that when the model lens is disposed along an intraocular lens plane of an eye model including a model cornea, the modulation transfer function of the eye model for the focus of the base power and the add power exceeds about 0.17, at a spatial frequency of about 50 line pairs per millimeter, over a range of at least 1.7 Diopters.

12. The intraocular lens of claim 11, wherein the modulation transfer function of the eye model exceeds about 0.20, at a spatial frequency of about 50 line pairs per millimeter, over a range of at least about 1.9 Diopters.

13. The intraocular lens of claim 1, wherein when the optic is placed in an intraocular lens plane of a physical eye model including a model cornea, the modulation transfer function of the eye model for the focus of the base power and the add power exceeds about 0.17, at a spatial frequency of about 50 line pairs per millimeter, over a range of at least about 1.7 Diopters.

14. The intraocular lens of claim 1, wherein the focus of the intraocular lens has a depth of focus, when illuminated by a light source, that is at least about 30% greater than that of an intraocular reference lens without the extended focus mask, the intraocular reference lens having a refractive power that is equal to the base power of the intraocular lens.

15. The intraocular lens of claim 1, further comprising a second optic disposed separate from the optic having the extended focus mask.

* * * * *